United States Patent
Saddow et al.

(10) Patent No.: US 11,185,261 B2
(45) Date of Patent: Nov. 30, 2021

(54) SYSTEM AND METHOD FOR NON-INVASIVE BLOOD GLUCOSE MONITORING

(71) Applicant: University of South Florida, Tampa, FL (US)

(72) Inventors: Stephen E. Saddow, Land O' Lakes, FL (US); Fabiola Araujo Cespedes, Temple Terrace, FL (US); Gokhan Mumcu, Tampa, FL (US); Christopher Leroy Frewin, Ann Arbor, MI (US)

(73) Assignee: University of South Florida, Tampa, FL (US)

( * ) Notice: Subject to any disclaimer, the term of this patent is extended or adjusted under 35 U.S.C. 154(b) by 406 days.

(21) Appl. No.: 16/262,836

(22) Filed: Jan. 30, 2019

(65) Prior Publication Data
US 2019/0231237 A1   Aug. 1, 2019

Related U.S. Application Data

(60) Provisional application No. 62/623,771, filed on Jan. 30, 2018.

(51) Int. Cl.
*A61B 5/145* (2006.01)
*A61B 5/0507* (2021.01)
(Continued)

(52) U.S. Cl.
CPC ........ *A61B 5/14532* (2013.01); *A61B 5/0507* (2013.01); *A61B 5/6813* (2013.01);
(Continued)

(58) Field of Classification Search
CPC .............. A61B 5/1455; A61B 5/14551; A61B 5/14532; A61B 5/742; A61B 5/6813; A61B 5/6833; A61B 5/6824
See application file for complete search history.

(56) References Cited

U.S. PATENT DOCUMENTS 8,882,670 B2 * 11/2014 Hancock ............ A61B 5/14532
600/309
9,198,607 B2 * 12/2015 Fischer ............... A61B 5/14532
(Continued)

OTHER PUBLICATIONS

Afroz, S. et al., Implantable SiC based RF antenna biosensor for continuous glucose monitoring, IEEE Sensors, Baltimore, Maryland USA, 2013.
(Continued)

*Primary Examiner* — Chu Chuan Liu
(74) *Attorney, Agent, or Firm* — Molly L. Sauter; Smith & Hopen, P.A.

(57) ABSTRACT

A system and method for continuous glucose monitoring (CGM) of blood in a blood vessel of a patient using a non-invasive sensor composed of a patch antenna operating in the Industrial, Scientific and Medical (ISM) Radio band (5.725 GHz-5.875 GHz). The device determines the blood glucose concentration of the blood in the blood vessel based on the measured shift of the resonant frequency of the non-invasive antenna patch sensor. A radio frequency (RF) synthesizer is used to drive the patch antenna with a fraction of its output coupled to both the antenna and receiver through a directional coupler. In this approach both the transmitted (FWD) and received (REV) power are processed, by demodulating logarithmic amplifiers, which convert the RF signals to corresponding voltages for downstream processing. The resulting voltages are then fed into a microcontroller and the measured shift in resonant frequency is converted to a real-time glucose concentration.

18 Claims, 3 Drawing Sheets

(51) Int. Cl.
  *H01Q 9/04* (2006.01)
  *A61B 5/00* (2006.01)
  *H01Q 1/27* (2006.01)

(52) U.S. Cl.
  CPC .............. *A61B 5/742* (2013.01); *H01Q 1/273* (2013.01); *H01Q 9/0407* (2013.01)

(56) References Cited

U.S. PATENT DOCUMENTS

| | | | |
|---|---|---|---|
| 2002/0049482 A1* | 4/2002 | Fabian | A61N 1/37 607/60 |
| 2012/0150000 A1* | 6/2012 | Al-Shamma'a | H01P 3/003 600/309 |
| 2015/0051466 A1 | 2/2015 | Afroz et al. | |

OTHER PUBLICATIONS

Afroz, S., A Biocompatible SiC RF Antenna for In-vivo Sensing Applications, Electrical Engineering, University of South Florida, 2013.

Frewin, C. L. et al., Single-Crystal Cubic Silicon Carbide: An in vivo biocompatible semiconductor for brain machine interface devices, Engineering in Medicine and Biology Society,EMBC, 2011 Annual International Conference of the IEEE, Boston, MA, 2011, pp. 2957-2960.

Frewin, C. L. et al., Silicon Carbide Neural Implants: in vivo Neural Tissue Reaction, Neural Engineering (NER), 6th International IEEE/EMBS Conference, Nov. 6-8, 2013, pp. 661-664.

Holt, P., Blood glucose monitoring in diabetes, Nursing Standard, Mar. 5, 2014, vol. 28, pp. 52-58.

So, C-F. et al., Recent advances in noninvasive glucose monitoring, Medical Devices (Auckland, N.Z.), Jun. 27, 2012, vol. 5, pp. 45-52.

\* cited by examiner

SYSTEM AND METHOD FOR NON-INVASIVE BLOOD GLUCOSE MONITORING

CROSS-REFERENCE TO RELATED APPLICATIONS

This application claims priority to U.S. Provisional Patent Application No. 62/623,771, entitled "Non-Invasive Blood Glucose Sensing", filed Jan. 30, 2018, by the same inventors, the entirety of which is incorporated herein by reference.

BACKGROUND OF THE INVENTION

1. Field of the Invention

This invention relates to medical devices. More specifically, it relates to a non-invasive blood glucose sensing system.

2. Brief Description of the State of the Art

The American Diabetes Association estimates that nearly 10% of the population in the United States has diabetes and that, by 2050, 1 in 3 Americans will have diabetes. Diabetes Mellitus is a metabolic disease in which the body is unable to produce or properly use insulin, leading to elevated glucose levels in the blood, known as hyperglycemia A person with frequent or extended episodes of hyperglycemia can suffer from complications in the nervous system, blood vessels and other organs, as well as heart disease, kidney disease, strokes, vision loss, and amputation. Therefore, maintaining a healthy glucose level is essential in a person's life.

Clinical studies have proven that self-monitoring of glucose levels helps treatment decisions in insulin and non-insulin use patients with diabetes. Although there are many instantaneous blood glucose monitors on the market, these provide only a single instantaneous level at that time, and multiple daily use of these devices leads to patient discomfort. Continuous monitoring of the blood sugar levels is much more useful, especially for individuals who are at high risk. All currently approved United States Food and Drug Administration (FDA) continuous glucose monitoring (CGM) devices require a disposable needle-like insertion into the body, which lasts only up to a week. In addition, CMG devices known in the art also require calibration four times a day utilizing a finger sticking blood sample technique, since the measurement is not done directly on the blood glucose, but rather measures the glucose of the interstitial fluid (ISF).

These CGM systems currently known in the art result in elevated costs, not only due to the device itself, but the cost of the disposable sensor needles, adding a monthly cost of around $300 per patient. Of course, the patient would prefer a less invasive method to monitor the glucose levels, and many have been tried, but have experienced various issues.

Most non-invasive glucose monitoring systems face the challenge of being susceptible to external interference from other factors such as body temperature, perspiration, skin moisture, changes in skin thickness and body movement. For instance, infrared spectroscopy, including near infrared (NIR) spectroscopy and far infrared (FIR) spectroscopy, depend upon optical transmission and reflection measurements, which are subject to interference from external factors that affect the reflection measurement. For this reason, near infrared (NIR) spectroscopy requires frequent recalibration.

In far infrared (FIR) spectroscopy, the emitted energy that is absorbed by glucose and measured is so small that this method has not yet been proven to be accurate. In other methods, such as Raman spectroscopy, the measurement of light scattering that is caused by generated oscillations, such as laser oscillations in the ocular fluid, is subject to interference from other molecules. In thermal spectroscopy, the infrared (IR) radiation that is emitted from the body is also affected by other factors, external to glucose concentration. Another example is the technology based on measuring the interstitial fluid (ISF) that is secreted from the skin to measure the glucose levels, which presents a time lag deficiency. Overall, non-invasive technologies lack accuracy due to being susceptible to external factors such as transpiration, temperature, positioning, and/or displaying time lag problems of up to twenty minutes, making the technology not yet reliable.

Another approach towards self-monitoring glucose is a fully implantable glucose monitoring system. These medical devices face other types of challenges such as in vivo inflammatory reaction and foreign body reaction, posing risk for the patients and hence the need for biocompatibility tests on any implantable device. Many implants have difficulties reliably functioning in vivo due to the inflammatory response to foreign materials, wherein the endpoint of this response may result in a close-knit encapsulation around the object, that is generally 100 microns thick, which not only acts as a diffusion barrier to enzymatic activity (as is used in current FDA approved CGM methods) but is also electrically insulating. Therefore, long-term implantations are subject to gradual loss of sensor functionality and stability due to fibrosis encapsulation and tissue changes in the proximity of the sensor.

Accordingly, what is needed in the art is a non-invasive glucose monitoring device that eliminates internal power and implantable electronics.

BRIEF SUMMARY OF THE INVENTION

In various embodiment, the present invention provides a system that allows for continuous glucose measurement (CGM) within the blood using a non-invasive device composed of a patch antenna operating in the Industrial, Scientific and Medical (ISM) Radio band (5.725 GHz-5.875 GHz) and circuitry to convert the measured resonant frequencies into glucose levels and to display the variation in glucose levels. The system determines the blood glucose concentration within a blood vessel of a patient based on the measured shift of the resonant frequency of the non-invasive antenna patch sensor.

In one embodiment, the present invention provides a non-invasive glucose monitoring system including, a patch antenna positioned exterior to a subject and aligned with a blood vessel of the subject and a radio frequency (RF) synthesizer to generate a radio frequency signal having a frequency sweep to drive the patch antenna. The system further includes, a first demodulating logarithmic amplifier, a second demodulating logarithmic amplifier and a bi-directional coupler. The bi-directional coupler is configured to receive the RF signal from the RF synthesizer and is further configured to transmit a fraction of the RF signal to the patch antenna, to transmit a forward coupled RF signal to the first demodulating logarithmic amplifier and to transmit a reverse coupled RF signal to the second demodulating logarithmic amplifier, wherein the first demodulating logarithmic amplifier is configured to convert the forward coupled RF signal to a corresponding forward voltage and the second demodulating logarithmic amplifier is configured to convert the reverse coupled RF signal to a corresponding reverse voltage. The system additionally includes, a microcontroller coupled to the first demodulating logarithmic amplifier and to the second demodulating logarithmic amplifier, the microcontroller to determine a glucose level of blood present in the blood vessel of the subject based upon the forward voltage and the reverse voltage.

The system may further include a display coupled to the microcontroller to visually display the blood glucose level.

In another embodiment, the present invention provides a method for non-invasive glucose monitoring. The method includes, positioning a patch antenna exterior to a subject and aligned with a blood vessel of the subject, generating a radio frequency signal having a frequency sweep at a radio frequency (RF) synthesizer, receiving the RF signal at a bi-directional coupler and transmitting, from the bi-directional coupler, a fraction of the RF signal to the patch antenna, a forward coupled RF signal to a first demodulating logarithmic amplifier and a reverse coupled RF signal to a second demodulating logarithmic amplifier. The method further includes, converting the forward coupled RF signal to a corresponding forward voltage at the first demodulating logarithmic amplifier, converting the reverse coupled RF signal to a corresponding reverse voltage at the second demodulating logarithmic amplifier and determining a glucose level of blood present in the blood vessel of the subject based upon the forward voltage and the reverse voltage.

As such, the present invention provides a non-invasive glucose monitoring device that eliminates internal power and implantable electronics.

BRIEF DESCRIPTION OF THE DRAWINGS

For a fuller understanding of the invention, reference should be made to the following detailed description, taken in connection with the accompanying drawings.

DETAILED DESCRIPTION OF THE INVENTION

Figure 1A:
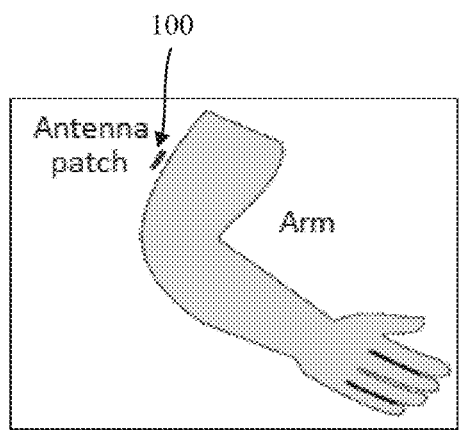
FIG. 1A illustrates a possible positioning of an antenna patch for a non-invasive glucose monitoring system, in accordance with an embodiment of the present invention.

In the following description, numerous specific details are set forth in order to provide a thorough understanding of the embodiments of the present disclosure. It will be apparent, however, to one skilled in the art that embodiments of the present disclosure may be practiced without some of these specific details. In some, well-known structures and devices are shown in block diagram form.

Embodiment of the present invention include various steps, which will be described below. The steps may be performed by hardware components or may be embodied in machine-executable instructions, which may be used to cause a general-purpose or special-purpose processor programmed with the instructions to perform the steps. Alternatively, the steps may be performed by a combination of hardware, software, firmware and/or by human operators.

Embodiments of the present invention may be provided as a computer program product, which may include a machine-readable storage medium tangibly including instructions, which may be used to program a computer or other electronic device to perform a process. The medium may include, but is not necessarily limited to, hard drives, magnetic tap, optical disks, read-only memories, programmable read-only memories, random access memories, flash memory and various other forms of media suitable for storing electronic instructions. Additionally, embodiments of the present invention may also be downloaded as one or more computer program products, wherein the program may be transferred from a remote computer to a requesting computer by way of transient signals via a communication link.

An apparatus for practicing various embodiments of the present invention may include one or more computers or processors and data storage systems containing or having access to computer programs coded in accordance with the various methods of performing the invention described herein, wherein the method steps can be accomplished using modules, routines, subroutines or subparts of a computer program product.

In various embodiments, the present invention provides a non-invasive blood glucose sensing system that is based on the glucose level induced shift in the resonant frequency of an antenna patch operating in the Industrial, Scientific and Medical (ISM) band (5.725-5.875 GHz). The measuring physical principle is based on variations of the resonant frequency of an antenna patch which is dependent upon the medium in which it is operating. It is known that an individual's blood permittivity is correlated to blood glucose levels. In the present invention, when the patch antenna is placed above the skin of a subject and in direct line of sight with a major blood vessel, the blood glucose level in the blood vessel affects the resonant frequency of the patch antenna. Therefore, placing a patch antenna in a fixed position at approximately 2 mm outside a person's skin and in direct line of sight with a major blood vessel, the patch antenna will experience a shift of resonant frequency that can be correlated to the variation of blood glucose levels. In general, by determining the shift of the resonant frequency of a properly place non-invasive patch antenna, one can determine the glucose levels present in the blood of a person of interest.

Figure 1B:
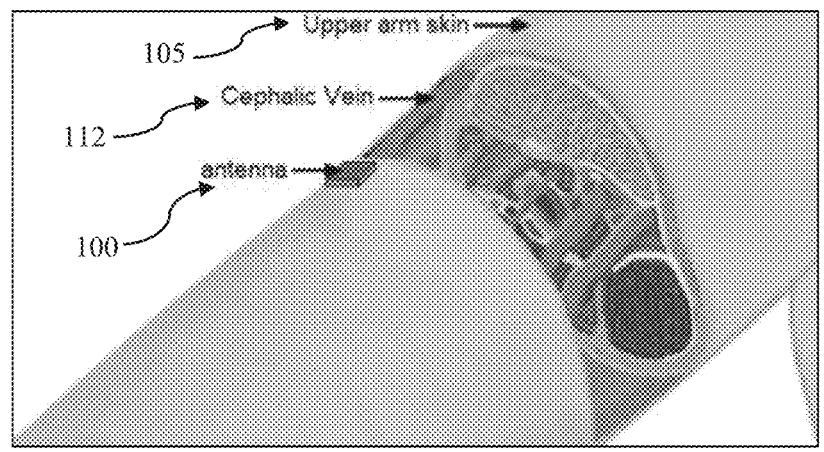
FIG. 1B illustrates an isometric, sectional view of a possible positioning of an antenna patch for a non-invasive glucose monitoring system, in accordance with an embodiment of the present invention.

With reference to FIG. 1A, a patch antenna 100 may be positioned on an arm of a subject or patient. The patch antenna 100 may be positioned directly onto the skin, or alternatively, the patch antenna 100 may include a substrate or standoff that allows the patch antenna 100 to be positioned above the surface of the skin. In one particular embodiment, the patch antenna is positioned approximately 2 mm above the surface of the skin. As further illustrated in FIG. 1B, in a particular embodiment, the antenna 100 may be positioned adjacent to the upper arm skin 105 and in line with a cephalic vein 112 of a subject of interest.

Figure 1C:
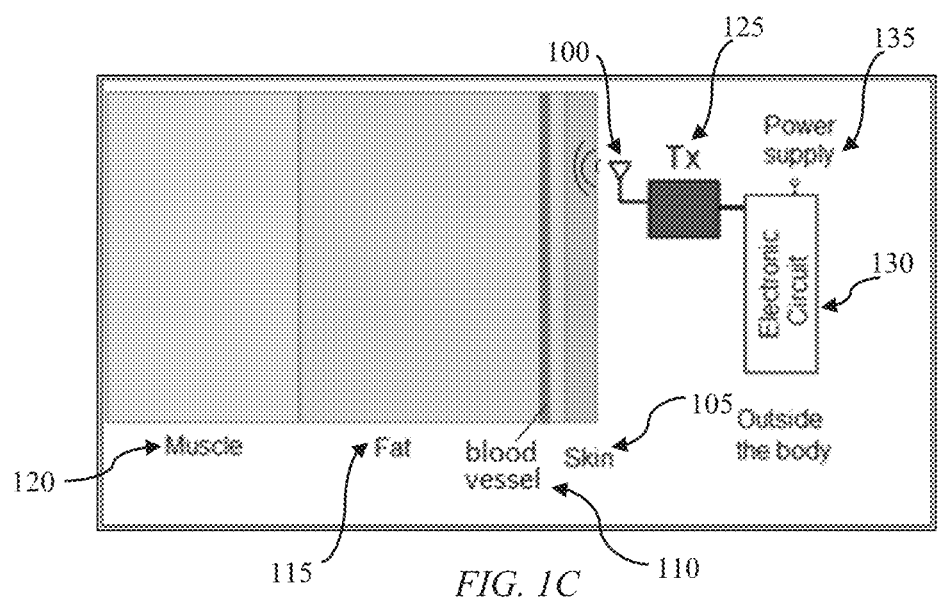
FIG. 1C illustrates an antenna patch position along with a sectional view of tissue showing the externally located sensing transmitter, in accordance with an embodiment of the present invention.

As shown in FIG. 1C, the arm of a subject includes a layer of muscle 120, a layer of fat 115, a layer of skin 105 and a blood vessel 110 positioned below the layer of skin 105. The patch antenna 100 is positioned close to the layer of skin 105 and in line with the blood vessel 110. The blood glucose monitoring device of the present invention includes, the patch antenna 100, a transmitter 125, electronic circuitry 130 and a power supply 135. The transmitter 125 may be a wireless transmitter and the electronic circuitry 130 and the power supply 135 are also positioned outside of the body of the subject. The interaction between the patch antenna 100 and the electronic circuitry 130 will be described in more detail below.

Figure 2A:
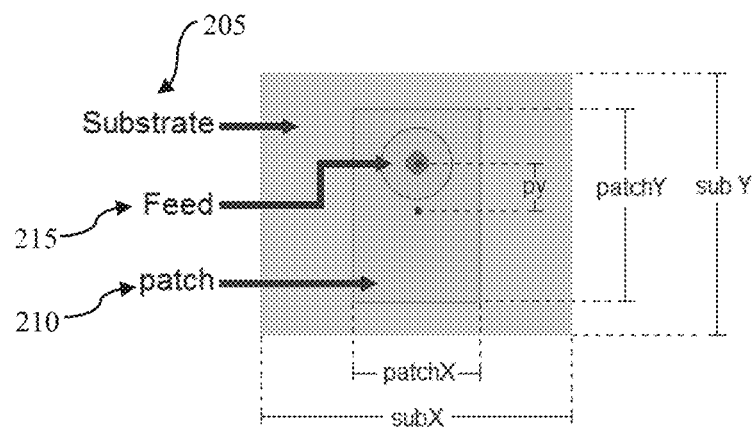
FIG. 2A is an isometric, sectional view of an arm showing an externally located antenna proximate to the Cephalic vein, in accordance with an embodiment of the present invention.
Figure 2B:
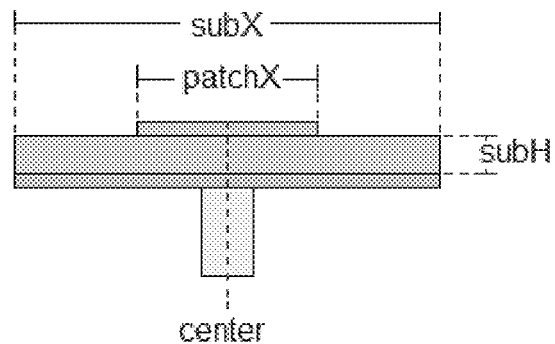
FIG. 2B shows a top cross-sectional view of the RF antenna, according to an embodiment of the present invention.
Figure 2C:
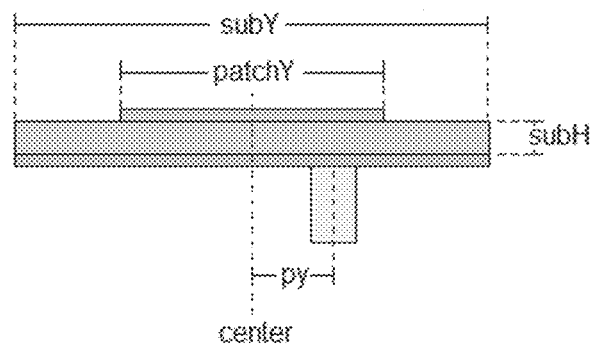
FIG. 2C shows a side cross-sectional view of the RF antenna, according to an embodiment of the present invention.

Various schematic views of the RF patch antenna in accordance with an embodiment of the present invention are illustrated with reference to FIG. 2A-FIG. 2C. The dimension variable identified in the figures are defined in Table 1. FIG. 2A is a top view of the RF antenna illustrating the dimension variables, the substrate 205, the patch antenna 210 and the feed 215 to the external circuitry. FIG. 2B is a cross-sectional view of side 1 (XY plane) of the RF antenna and FIG. 2C is a cross-sectional view of side 2 (YZ plane) of the RF antenna.

TABLE 1

Exemplary antenna dimensions for non-invasive blood glucose sensing

| Parameter | subX | subY | patchX | patchY | subH | px | Py |
|---|---|---|---|---|---|---|---|
| Dimension | 2.4 cm | 1.9 cm | 3.7 mm | 7.9 mm | 25 mil | 0.0 mm | 1.5 |

In an exemplary embodiment, the RF patch antenna is designed using a 635 μm thick substrate ($\varepsilon_r$=10.2, tan δ=0.0023) with the geometry design and dimensions shown in Table 1, corresponding to the diagrams in FIG. 2A-FIG. 2C. However, this design and dimensions are not intended to be limiting and various other designs and dimensions of the RF patch antenna are within the scope of the present invention.

Figure 3:
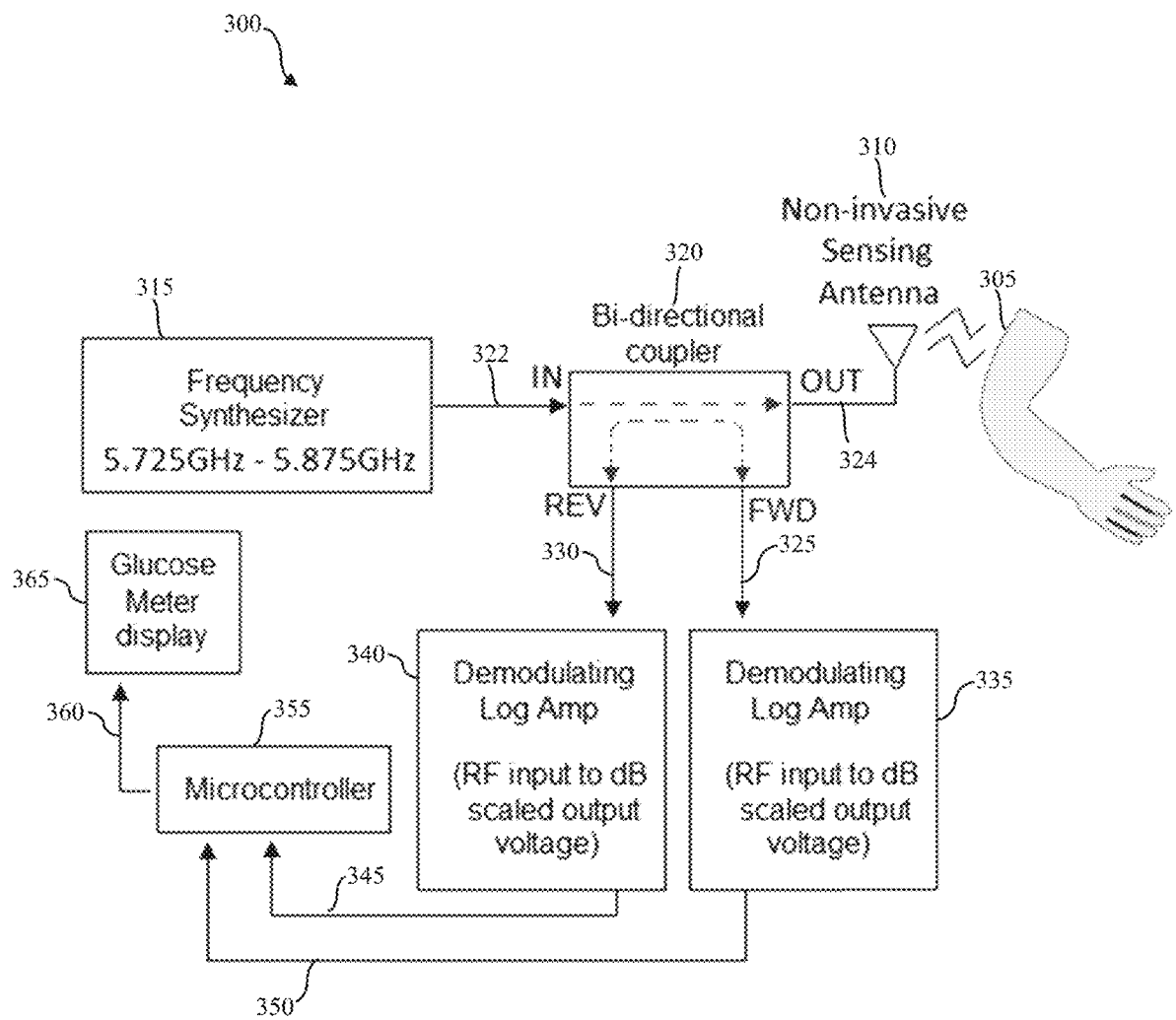
FIG. 3 is a block diagram of the non-invasive blood glucose monitoring system, in accordance with an embodiment of the present invention.

A block diagram illustrating an embodiment of the non-invasive blood glucose monitor of the present invention is shown in FIG. 3. In this embodiment, the blood glucose monitoring system 300 includes a non-invasive sensing antenna 310, a frequency synthesizer 315, a bi-directional coupler 320, a first demodulating logarithmic amplifier 340 and a second demodulating logarithmic amplifier 335, a microcontroller 355 and a glucose meter display 365.

Radio frequency (RF) synthesizers 315 are well known in the art for generating RF signals to drive an antenna element. In this particular embodiment, the RF synthesizer 315 generates an RF signal that sweeps between about 5.725 GHz and about 5.875 GHz, at 1 MHz intervals.

Bi-directional couplers, such as the bi-directional coupler 320 of the present invention, are also well known in the art for operating with a specific frequency range as a four-port network in with the traveling signal from the forward 322 (IN port) and the reverse 324 (OUT port) are coupled to two ports, FWD coupled port 325 and REV coupled port 330. In operation of the bi-directional coupler 320, a portion of the signal from the IN port 322 to the OUT port 324 is coupled to the FWD coupled port 325, but not to the REV coupled port 330, and a portion of the OUT port 324 is coupled to the REV coupled port 330, but not to the FWD coupled port 325. A first demodulating logarithmic amplifier 335 is coupled to the FWD coupled port 325 of the bi-directional coupler 320 and a second demodulating logarithmic amplifier 340 is coupled to the REV coupled port 330 of the bi-directional coupler 320.

Demodulating logarithmic amplifiers are known in the art and may also be referred to as logarithmic converters. In general, demodulating logarithmic amplifiers compress a received signal of wide range to its decibel equivalence, thus converting the signal form one domain to another through a precise nonlinear transformation. In the present invention, the first demodulating logarithmic amplifier 335 receives an RF signal from the FWD coupled port 325 of the bi-directional coupler 320 and converts the RF signal to a corresponding decibel-scaled forward voltage and the second demodulating logarithmic amplifier 340 receives an RF signal from the REV coupled port 330 and converts the RF signal to a corresponding decibel-scaled reverse voltage.

The microcontroller 355 of the present invention includes various circuitry for generating a blood glucose level from the forward voltage and reverse voltage. In one embodiment, the microcontroller 355 includes an analog to digital to digital converter and is programmed to calculate an estimate of the glucose level based on the forward voltage and the reverse voltage.

In operation of the glucose monitoring device 300, the RF synthesizer 315 is used to drive the non-invasive patch antenna 310 that is positioned close to the skin 305, and in line with a blood vessel, of a subject. The RF synthesizer 315 drives the patch antenna in the ISM band, generating frequencies from 5.725 GHz to 5.875 GHz in intervals of 1 MHz. The RF signal enters the bi-directional coupler 320 at an input port 322 with a nominal coupling of 6 dB and a forward directivity of 23 dB. The bi-directional coupler 320 is used to obtain continuous power reflection measurements from the non-invasive antenna 310, relative to the forward power for each frequency at its input 322. A fraction of the output 324 of the bi-directional coupler 420 is coupled to both the antenna and receiver through a directional coupler. In this approach both the transmitted (FWD) 325 and received (REV) 330 power are processed by demodulating logarithmic amplifiers 335, 340 which convert the RF signals to corresponding voltages for downstream processing. In particular, the forward coupled signal 325 and the reverse coupled signal 330 are fed separately to demodulating logarithmic amplifiers 335, 340 to convert the RF input signal to a decibel-scaled output voltage with a nominal logarithmic slope of −25 mV/dB. Both outputs 345, 350 from the demodulating logarithmic amplifiers 335, 340 are then fed into a microcontroller 355 and the measured shift in resonant frequency, $f_0$, is converted to a real-time glucose concentration 360 which is displayed on the glucose meter display 365. By implementing this system architecture an accurate, real-time assessment of blood glucose level can be made using a single sense antenna.

The non-invasive blood glucose monitoring device was tested experimentally by using oil in gel phantoms to mimic the electrical properties of skin, fat, blood and muscle in a human tissue model and placing the antenna above the mimicking skin. For blood phantom variation of 2000 mg/dL D-glucose in the phantom mixture, the relative permittivity of the phantom decreased from 52.635 to 51.482, which resulted in a shift of resonant frequency from 5.855 to 5.842 (i.e., a 13 MHz shift). This is consistent with the non-invasive simulated results using ANSYS HFSS™, where simulated blood permittivity variation of 51.397 to 52.642 resulted in a shift of resonant frequency from 5.797 to 5.807 (i.e., a 10 MHz shift). While this variation in blood glucose is non-physical (typical human glucose range can range in the extremes from 30 to 400 mg/dL, where healthy glucose levels vary from 70 mg/dL to 180 mg/dL) it was necessary to provide a high confidence fit between the simulated and experimental data, thus the reason of the expanded range of blood phantom and simulated glucose levels range.

Accordingly, the present invention provides a system and method for continuous glucose monitoring (CGM) of blood in a blood vessel of a patient using a non-invasive sensor composed of a patch antenna. The device determines the blood glucose concentration of the blood in the blood vessel based on the measured shift of the resonant frequency of the non-invasive antenna patch sensor.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

What is claimed is:

1. A non-invasive glucose monitoring system, the system comprising:
    a patch antenna configured to be positioned exterior to a subject and aligned with a cephalic vein of an upper arm of the subject;
    a radio frequency (RF) synthesizer to generate a radio frequency signal having a frequency sweep, wherein the frequency sweep of the RF synthesizer is between about 5.725 GHz and about 5.875 GHz at 1 MHz intervals;
    a first demodulating logarithmic amplifier and a second demodulating logarithmic amplifier;
    a bi-directional coupler to receive the RF signal from the RF synthesizer, to transmit a fraction of the RF signal to the patch antenna, and to transmit a forward coupled RF signal to the first demodulating logarithmic amplifier;
    the bi-directional coupler further to receive a reverse coupled RF signal comprising continuous power reflection measurements from the patch antenna in response to the frequency sweep of the RF synthesizer and to transmit the reverse coupled RF signal to the second demodulating logarithmic amplifier;
    the first demodulating logarithmic amplifier to convert the forward coupled RF signal to a corresponding forward voltage and the second demodulating logarithmic amplifier to convert the reverse coupled RF signal to a corresponding reverse voltage; and
    a microcontroller coupled to the first demodulating logarithmic amplifier and to the second demodulating logarithmic amplifier, the microcontroller to determine a glucose level of blood present in the cephalic vein of the upper arm of the subject based upon the forward voltage and the reverse voltage.

2. The system of claim 1, wherein the patch antenna is configured to be placed in contact with the subject's outer skin of the upper arm.

3. The system of claim 1, wherein the patch antenna further comprises a substrate that is configured to be placed in contact with the subject's outer skin of the arm such that the patch antenna is positioned above the subject's outer skin of the arm.

4. The system of claim 1, wherein the bi-directional coupler has a nominal coupling of 6 dB and a forward directivity of 23 dB.

5. The system of claim 1, wherein the forward voltage is a decibel-scaled output voltage from the bi-directional coupler having a nominal logarithmic solve of −25 mV/dB and the reverse voltage is a decibel-scaled output voltage from the bi-directional coupler having a nominal logarithmic solve of −25 mV/dB.

6. The system of claim 1, wherein the microcontroller determines a glucose level of blood present in the cephalic vein of the upper arm of the subject based upon the forward voltage and the reverse voltage by calculating a difference between the forward voltage and the reverse voltage at each of the sweeping frequencies to identify a resonant frequency of the patch antenna.

7. The system of claim 1, further comprising a display coupled to the microcontroller, the display for visually displaying the measured glucose level.

8. A non-invasive glucose monitoring system, the system comprising:
    a patch antenna configured to be positioned exterior to a subject and aligned with a cephalic vein of an upper arm of the subject;
    a radio frequency (RF) synthesizer to generate a radio frequency signal having a frequency sweep between about 5.725 GHz and about 5.875 GHz at 1 MHz intervals;
    a first demodulating logarithmic amplifier and a second demodulating logarithmic amplifier;
    a bi-directional coupler to receive the RF signal from the RF synthesizer, to transmit a fraction of the RF signal to the patch antenna, and to transmit a forward coupled RF signal to the first demodulating logarithmic amplifier;
    the bi-directional coupler further to receive a reverse coupled RF signal comprising continuous power reflection measurements from the patch antenna in response to the frequency sweep of the RF synthesizer and to transmit the reverse coupled RF signal to the second demodulating logarithmic amplifier;
    the first demodulating logarithmic amplifier to convert the forward coupled RF signal to a corresponding forward voltage and the second demodulating logarithmic amplifier to convert the reverse coupled RF signal to a corresponding reverse voltage;
    a microcontroller coupled to the first demodulating logarithmic amplifier and to the second demodulating logarithmic amplifier, the microcontroller to determine a glucose level of blood present in the cephalic vein of the upper arm of the subject based upon the forward voltage and the reverse voltage;
    a display for visually displaying the glucose level determined by the microcontroller.

9. The system of claim 8, wherein the patch antenna is configured to be placed in contact with the subject's outer skin of the upper arm.

10. The system of claim 8, wherein the display is a liquid crystal display (LCD) coupled to the microcontroller.

11. A method for non-invasive glucose monitoring, the method comprising:
    positioning a patch antenna exterior to a subject and aligned with a cephalic vein of an upper arm of the subject;
    generating a radio frequency (RF) signal having a frequency sweep at a radio frequency (RF) synthesizer, wherein the frequency sweep of the RF synthesizer is between about 5.725 GHz and about 5.875 GHz at 1 MHz intervals;
    receiving the RF signal at a bi-directional coupler;

transmitting, from the bi-directional coupler, a fraction of the RF signal to the patch antenna, a forward coupled RF signal to the first demodulating logarithmic amplifier;

receiving, at the bi-directional coupler, a reverse coupled RF signal comprising continuous power reflection measurements from the patch antenna in response to the frequency sweep of the RF synthesizer and transmitting, from the bi-directional coupler the reverse coupled RF signal to the second demodulating logarithmic amplifier;

converting the forward coupled RF signal to a corresponding forward voltage at the first demodulating logarithmic amplifier;

converting the reverse coupled RF signal to a corresponding reverse voltage at the second demodulating logarithmic amplifier; and determining a glucose level of blood present in the cephalic vein of the upper arm of the subject based upon the forward voltage and the reverse voltage.

12. The method of claim 11, further comprising placing the patch antenna in contact with the subject's outer skin and in line with a cephalic vein of an arm of the subject.

13. The method of claim 11, wherein the patch antenna further comprises a substrate, and wherein the method further includes placing the substrate in contact with the subject's outer skin of the upper arm such that the patch antenna is positioned above the subject's outer skin of the upper arm.

14. The method of claim 11, wherein the bi-directional coupler has a nominal coupling of 6 dB and a forward directivity of 23 dB.

15. The method of claim 11, wherein the forward voltage is a decibel-scaled output voltage from the bi-directional coupler having a nominal logarithmic solve of −25 mV/dB and wherein the reverse voltage is a decibel-scaled output voltage from the bi-directional coupler having a nominal logarithmic solve of −25 mV/dB.

16. The method of claim 11, wherein determining a glucose level of blood present in the cephalic vein of the upper arm of the subject based upon the forward voltage and the reverse voltage is performed by a microcontroller.

17. The method of claim 11, wherein determining a glucose level of blood present in the cephalic vein pf the upper arm of the subject based upon the forward voltage and the reverse voltage further comprises calculating a difference between the forward voltage and the reverse voltage at each of the sweeping frequencies to identify a resonant frequency of the patch antenna.

18. The method of claim 11, further comprising displaying the measured glucose level on a visual display.

* * * * *